(12) United States Patent
van Spronsen et al.

(10) Patent No.: US 9,938,547 B2
(45) Date of Patent: Apr. 10, 2018

(54) PROCESS FOR THE PREPARATION OF 2,5-FURANDICARBOXYLIC ACID

(71) Applicant: Technische Universiteit Delft, Delft (NL)

(72) Inventors: Jacob van Spronsen, Delft (NL); Geert-Jan Witkamp, Delft (NL); Bart de Graaff, Delft (NL)

(73) Assignee: TECHNISCHE UNIVERSITEIT DELFT (NL)

( * ) Notice: Subject to any disclaimer, the term of this patent is extended or adjusted under 35 U.S.C. 154(b) by 0 days.

(21) Appl. No.: 14/900,182

(22) PCT Filed: Jun. 20, 2014

(86) PCT No.: PCT/NL2014/050411
§ 371 (c)(1),
(2) Date: Dec. 21, 2015

(87) PCT Pub. No.: WO2014/209112
PCT Pub. Date: Dec. 31, 2014

(65) Prior Publication Data
US 2016/0145662 A1    May 26, 2016

(30) Foreign Application Priority Data
Jun. 24, 2013  (NL) .................................... 2011027

(51) Int. Cl.
*C12P 17/04* (2006.01)
*C07D 307/68* (2006.01)

(52) U.S. Cl.
CPC ............ *C12P 17/04* (2013.01); *C07D 307/68* (2013.01)

(58) Field of Classification Search
None
See application file for complete search history.

(56) References Cited

FOREIGN PATENT DOCUMENTS

| EP | 1094047 A1 | 4/2001 |
|----|------------|--------|
| WO | 2008113395 A1 | 9/2008 |
| WO | 2009023174 A2 | 2/2009 |
| WO | 2011026913 A1 | 3/2011 |
| WO | 2012064195 A2 | 5/2012 |
| WO | 2013025106 A1 | 2/2013 |

OTHER PUBLICATIONS

Koopman et al., "Efficient Whole-Cell Biotransformation of 5-(hydroxymethyl) furfural into FDCA, 2,5-furandicarboxylic acid" Bioresource Technology, 2010, pp. 6291-6296.
International Search Report and Written Opinion to the corresponding Int'l patent application No. PCT/NL2014/050411, 10 pages.

*Primary Examiner* — Rebecca E Prouty
(74) *Attorney, Agent, or Firm* — Tarolli, Sundheim, Covell & Tummino LLP

(57) ABSTRACT

The invention is directed to a process for the preparation of 2,5-furandicarboxylic acid (FDCA) by fermentation comprising fermenting a suitable starting compound to produce an aqueous solution of a salt of FDCA having a pH of at least 7, optionally removing solids from said solution, e.g. by filtration, subsequently freeze crystallizing the said salt of FDCA from said solution at said pH, isolating the said FDCA salt in the form of solid crystals, preparing an aqueous solution of said salt and crystallizing FDCA as the free acid from said solution at an acidic pH.

7 Claims, 1 Drawing Sheet

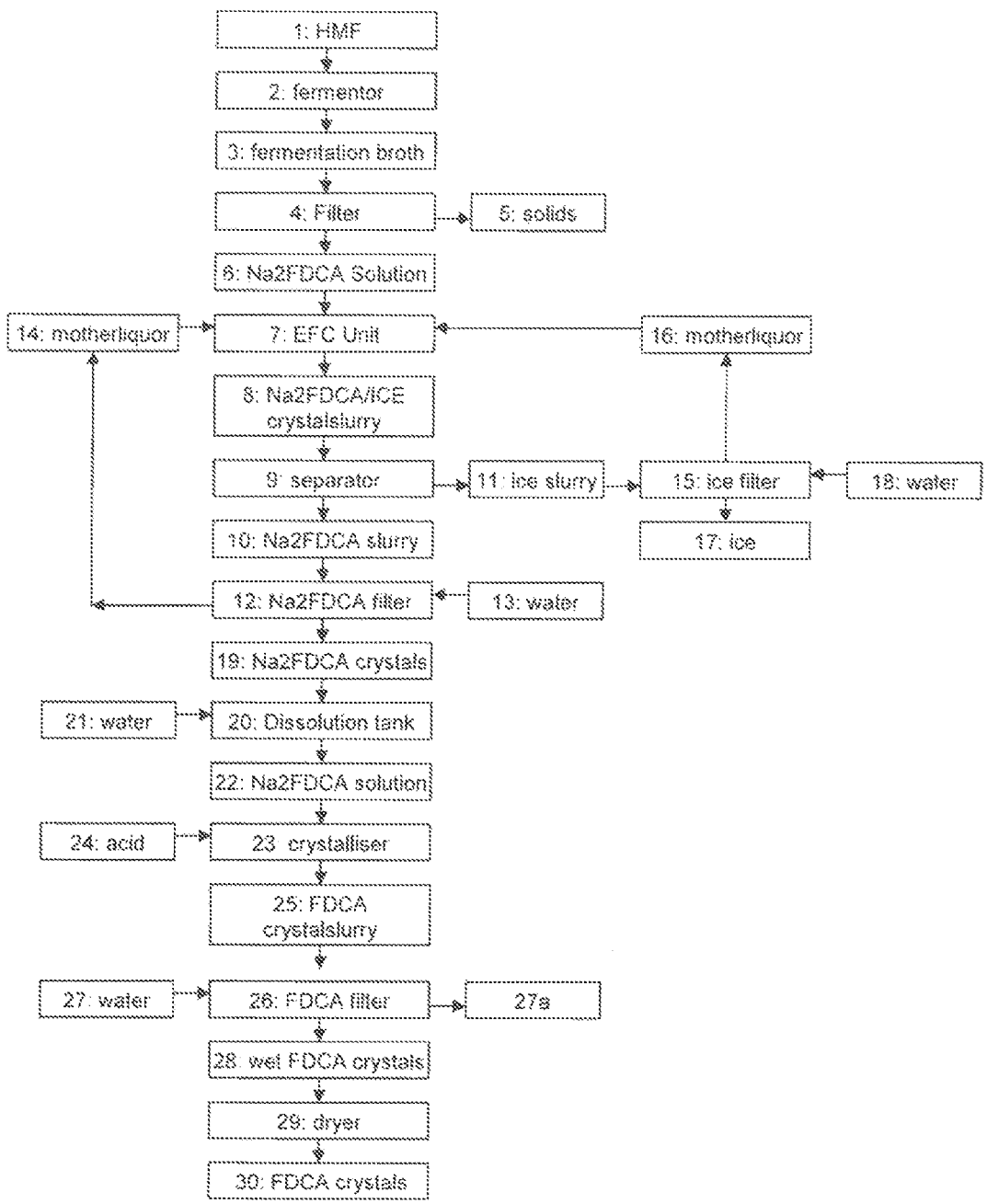

PROCESS FOR THE PREPARATION OF 2,5-FURANDICARBOXYLIC ACID

RELATED APPLICATIONS

The present application is a U.S. National Stage under 35 USC 371 patent application, claiming priority to Serial No. PCT/NL2014/050411, filed on Jun. 20, 2014, which claims priority from NL 2011027, filed on Jun. 24, 2013, the entirety of both of which are incorporated herein by reference.

FIELD OF THE INVENTION

The invention is directed to a process for producing 2,5 furan dicarboxylic acid (FDCA) by fermentation followed by purification of the resulting fermentation broth to produce substantially pure FDCA as the free acid.

BACKGROUND OF THE INVENTION

FDCA is a very promising compound which can be produced via biological pathways and which is a useful starting compound for various chemical compounds.

Various methods for the production of FDCA are known, some of them by various chemical synthesis steps, others by fermentation of suitable starting compounds, such as hydroxymethyl furfural (HMF) (WO 2012/064195).

One of the disadvantages of the enzymatic preparation of FDCA is the difficulty of removing contaminants from the product to produce a substantially pure FDCA. More in particular it has been found to be very difficult to remove the monocarboxylic acid from the final product, for example when using the conventional acid precipitation.

It is one of the objects of the invention to provide a process for producing substantially pure FDCA by fermentation having a very low mono carboxylic acid content.

SUMMARY OF THE INVENTION

The invention is accordingly directed to a process for the preparation of 2,5-furandicarboxylic acid (FDCA) by fermentation comprising fermenting a suitable starting compound to produce an aqueous solution of a salt of FDCA having a pH of at least 7, optionally removing solids from said solution, e.g. by filtration, subsequently freeze crystallizing the said salt of FDCA from said solution at said pH, isolating the said FDCA salt in the form of solid crystals, preparing an aqueous solution of said salt and crystallizing FDCA as the free acid from said solution at an acidic pH in a crystallizer by adding at least one acid to said solution of the salt of FDCA to provide for the acidic pH, wherein either the crystallizer already contains an amount of aqueous liquid to which the solution and the acid are added, or the aqueous solution and the acid are added simultaneously to the crystallizer.

The process of the invention has the very important and unexpected advantage of providing FDCA in very high purity, almost completely free of the mono carboxylic acid.

The present invention comprises various steps, namely first the fermentation to produce a fermentation broth containing a salt of FDCA. Pretreatment of the fermentation broth like sterilization, centrifugation and decolourization is subsequently done to remove cell lysis and solid particles (if necessary) before carrying out the crystallization experiments.

The resulting aqueous solution is subjected to freeze crystallization, preferably eutectic freeze crystallization. The products of this are ice crystals, FDCA salt crystals and a mother liquor. The FDCA salt is then dissolved to produce an aqueous solution. From this solution FDCA is crystallized as the free acid under acidic conditions.

There are various ways to crystallize FDCA as the free acid from the said solution. An important aspect thereby is that the pH is at an acidic value, preferably below pH of 3. One method is the addition of a salt to the said solution. By the lowering of the pH value the free salt of FDCA crystallizes. Another method is the simultaneous addition of the salt and an acid (or acidic solution). A preferred way of crystallizing is to provide an amount of water in the crystallizer, to which simultaneously the salt solution and the acid are added. It has been found that this method, contrary to direct addition of acid to the salt solution, produces crystals of the free acid of FDCA without inclusions of contaminants in the crystals.

The FDCA crystals are then separated from the mother liquor, which also contains dissolved salt, as will be explained later. The crystals may be washed to remove mother liquor. The mother liquor may be treated in a conventional way to remove or recover the said salt and to produce water, for example by eutectic freeze crystallization or another method. In case the salt is useful (as will be discussed below) it may be reused in the process.

The production of FDCA starts via the bio-catalytic conversion of suitable starting materials, such as 5-hydroxymethylfurfural [HMF].

In that case this can be done by aerobic growth of Gram-negative bacterium *Cupriavidus basilensis*. This is can be carried out in a batch seed fermenter or in a continuous main fermenter at constant temperature (for example between 30 and 37° C.).

The fermentation occurs at a pH of 7 or higher by the addition of at least one alkaline compound, such as sodium hydroxide, sodium bicarbonate or ammonia.

The resulting fermentation broth is then treated to make it suitable for the recovery of the FDCA from it. This treatment generally includes removal of solids, possibly sterilization, and decolourization.

From the aqueous solution, a salt of FDCA is then preferably recovered by eutectic freeze crystallization, which is a process based on separation of components at a eutectic freezing point. Eutectic freeze crystallisation has been described in EP-A 1,230,194 and in Chem. Eng. Proc. 37, (1998), pp 207-213.

In freeze crystallisation at a eutectic freezing point (Eutectic freeze crystallisation: EFC) on the one hand the crystalline salt of FDCA is obtained, and on the other hand ice crystals. Depending on the nature of the cation of the alkaline compound used in the fermentation, the corresponding salt is obtained.

The crystals of the FDCA salt (generally sodium or ammonium salt), optionally after washing, for example with water or a saturated FDCA salt solution, are redissolved in water and subsequently the free acid is crystallized from the aqueous solution of the FDCA salt. As indicated above, various methods may be used for this, but the preferred way is the simultaneous injection of acid and the FDCA salt solution into a crystallizer.

The free acid of FDCA is crystallized and a salt solution is obtained. Depending on the nature of the cations of the FDCA salt and the acid used, a specific salt is produced. In case of sodium and the use of sulphuric acid, a sodiumsulfate solution is obtained. This solution may be treated, for example by EFC, to produce solid sodium sulphate and water. In the case of ammonia, ammonium sulphate is obtained. When carbon dioxide is used to acidify, sodium bicarbonate is obtained. It is for example possible to recycle this to the fermentation step to keep the pH at the correct level.

The FDCA crystals can be separated from the mother liquor (salt solution) and washed to remove remaining, adhering salt.

BRIEF DESCRIPTION OF THE DRAWINGS

FIG. 1 is a flow sheet showing one variant of the process.

DETAILED DESCRIPTION OF THE INVENTION

The invention is now further explained on the basis of the attached FIG. 1, showing a flow sheet of one variant of the process.

In the FIG. 1, HMF is fed via line 1 to a fermenter 2. The fermentation broth is introduced via line 3 into filtration unit 4 to remove solids from the broth. The solids are removed via line 5. The clear solution is introduced via line 6 into eutectic freeze crystallization unit 7. The Na$_2$FDCA/Ice slurry obtained therein is introduced via line 8 into separator 9. In the separator ice slurry is removed with part of the mother liquor and introduced via line 11 into filter 15. The ice crystals are washed with water via line 18 and are removed from the system via line 17.

The remaining Na$_2$FDCA slurry, comprising Na$_2$FDCA crystals in mother liquor, is fed from separator 9 into filter 12, via line 10 and washed, introduced into filter 12, via line 13. The mother liquor is recycled via line 14 to EFC unit 7. If necessary a small bleed stream may be used to remove part of the mother liquor from line 14 or 16, to prevent build-up of contaminants in the system.

The Na$_2$FDCA crystals are preferably washed with water or a saturated Na$_2$FDCA solution (to minimalize losses a saturated solution is preferred) and fed via line 19 into dissolution tank 20, wherein the Na$_2$FDCA salt crystals are dissolved in water, introduced via line 21. The FDCA solution thus obtained, is introduced in crystallizer 23, via line 22. Acid or an acidic solution is introduced simultaneously via line 24 into crystallizer 23.

In the crystallizer, crystals of the free acid of FDCA dispersed in an aqueous salt solution are obtained. This dispersion is introduced via line 25 into separation unit 26, where it is filtered or centrifuged to produce the free acid crystals and a mother liquor (salt solution). The crystals are washed with water introduced via line 27. The mother liquor and wash liquor are removed via line 27$^a$. The product crystals are obtained via line 28. If required they may be dried in dryer 29. The crystals are removed from the dryer via line 30.

The invention is now elucidated on the basis of the following, non-limiting examples.

Example 1

Isolation of the Disodium Salt of FDCA from Fermentation Broth.

*P. Putida* S12 equipped with the hmfH oxidoreductase gene from bacterium *Cupriavidus basilensis* was fermented in a fedbatch experiment for the production of FDCA from HMF. Glycerol and HMF were fed into the fermentor. The pH was maintained at 7 with 10 N NaOH. Dissolved oxygen tension was maintained at 30% air saturation. Temperature was kept at 25° C. After the fermentation the solids were removed by centrifugation. 1 l. Of the resulting solution was cooled down. At −6° C. ice started to crystallise from the solution. At the eutectic point at −7° C. a second solid, the disodium salt of FDCA, started to crystallize from solution. After cooling for another hour at −7° C. the crystals of the disodium salt of FDCA were removed from the crystallisation mixture by filtration. The crystals of the disodium salt of FDCA were washed with 50 ml of a saturated disodium FDCA solution resulting in 30 gram of wet crystals.

Recrystallization of the Disodium Salt of FDCA into FDCA.

10 Gram of the disodium salt of FDCA was dissolved in 100 ml. of water. The resulting solution was added to 50 ml. of water over 1 hour at 25° C. The pH of water phase was kept at 1 with 6N sulphuric acid. After stirring for another hour at 25° C. 5 gram of substantially pure FDCA crystals were isolated by filtration, washing with 30 ml of water and drying on the air at 50° C. The purity of the FDCA crystals was >99% with the content of 5-(hydroxymethyl)furoic acid <0.1%.

Example 2 (Comparative)

Direct Isolation of FDCA from Fermentation Broth.

*P. Putida* S12 equipped with the hmfH oxidoreductase gene from bacterium *Cupriavidus basilensis* was fermented in a fedbatch experiment for the production of FDCA from HMF. Glycerol and HMF were fed into the tormentor. The pH was maintained at 7 with 10 N NaOH. Dissolved oxygen tension was maintained at 30% air saturation. Temperature was kept at 25° C. After the fermentation the solids were removed by centrifugation. 1 l. of the resulting solution was added to 50 ml. of water over 1 hour at 25° C. The pH of water phase was kept at 1 with 6N sulphuric acid. After stirring for another hour at 25° C. 15 gram of FDCA crystals were isolated by filtration, washing with 30 ml of water and drying on the air at 50° C. The purity of the FDCA crystals was 87% with the content of 5-(hydroxymethyl)furoic acid 1%.

Comparing this result with the result of the process according to the invention, as exemplified in Example 1, it is clear that there is a marked and important improvement in the purity of the fin al product, FDCA.

The invention claimed is:

1. Process for the preparation of 2,5-furandicarboxylic acid (FDCA) by fermentation comprising fermenting a starting compound of 5-hydroxy methyl furfural (HMF) with a *Cuprividus basilensis* hmfH oxidoreductase to produce an aqueous solution of a salt of FDCA having a pH of at least 7, optionally removing solids from said solution, subsequently freeze crystallizing the said salt of FDCA from said solution at said pH, isolating the said FDCA salt in the form of solid crystals, preparing an aqueous solution of said salt and crystallizing FDCA as the free acid from said solution at an acidic pH; and wherein the crystallization of the free acid of FDCA produces a salt solution as mother liquor, which salt is sodium bicarbonate, and which is at least partly recycled to the fermentation.

2. Process according to claim 1, wherein the crystallization of the free acid of FDCA is done at a pH below 3.

3. Process according to claim 1, wherein at least one acid is added to said solution of the salt of FDCA to provide for an acidic pH.

4. Process according to claim 1, wherein the crystallization of the free acid of the FDCA is done by adding the aqueous solution and an acid simultaneously to a crystallizer.

5. Process according to claim 4, wherein the crystallizer already contains an amount of aqueous liquid to which the solution and the acid are added.

6. Process according to claim 1, wherein the freeze crystallization of the FDCA salt is done at the eutectic freezing point of the solution.

7. Process according to claim 1, wherein solids are removed from the aqueous solution of a salt of FDCA having a pH of at least 7, by filtration.

* * * * *